United States Patent
Lam et al.

(10) Patent No.: US 9,072,619 B2
(45) Date of Patent: Jul. 7, 2015

(54) PREFERENTIALLY ELECTROPOLISHED STENT SYSTEM AND METHOD OF MANUFACTURE

(71) Applicant: Medtronic Vascular, Inc., Santa Rosa, CA (US)

(72) Inventors: Rui Lam, Santa Rosa, CA (US); Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 394 days.

(21) Appl. No.: 13/705,842

(22) Filed: Dec. 5, 2012

(65) Prior Publication Data

US 2014/0155979 A1 Jun. 5, 2014

(51) Int. Cl.
*A61F 2/06* (2013.01)
*A61F 2/82* (2013.01)
*C25F 3/16* (2006.01)

(52) U.S. Cl.
CPC ... *A61F 2/82* (2013.01); *C25F 3/16* (2013.01); *A61F 2240/001* (2013.01); *A61F 2250/0025* (2013.01)

(58) Field of Classification Search
CPC . A61F 2/91; A61F 2/915; A61F 2002/91558; A61F 2/0077; A61F 2/90; A61F 2002/9154; A61F 2/86; A61F 2240/001; A61F 2250/0025; A61F 2/82; C25F 3/16
USPC .................................. 623/1.11, 1.15
See application file for complete search history.

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau | |
| 6,090,127 A | 7/2000 | Globerman | |
| 6,136,023 A | 10/2000 | Boyle | |
| 6,579,310 B1 * | 6/2003 | Cox et al. | 623/1.16 |
| 2003/0028241 A1 * | 2/2003 | Stinson | 623/1.15 |

* cited by examiner

*Primary Examiner* — Katherine M Shi

(57) ABSTRACT

The preferentially electropolished stent system and method of manufacture includes a stent delivery system including a catheter; a balloon operably attached to the catheter; and a stent disposed on the balloon. The stent includes an elongate body having an abluminal surface and a luminal surface; wherein the abluminal surface has an abluminal average roughness less than or equal to 0.030 microns; and the luminal surface has at least one rough portion having a luminal average roughness greater than or equal to 0.036 microns.

18 Claims, 11 Drawing Sheets

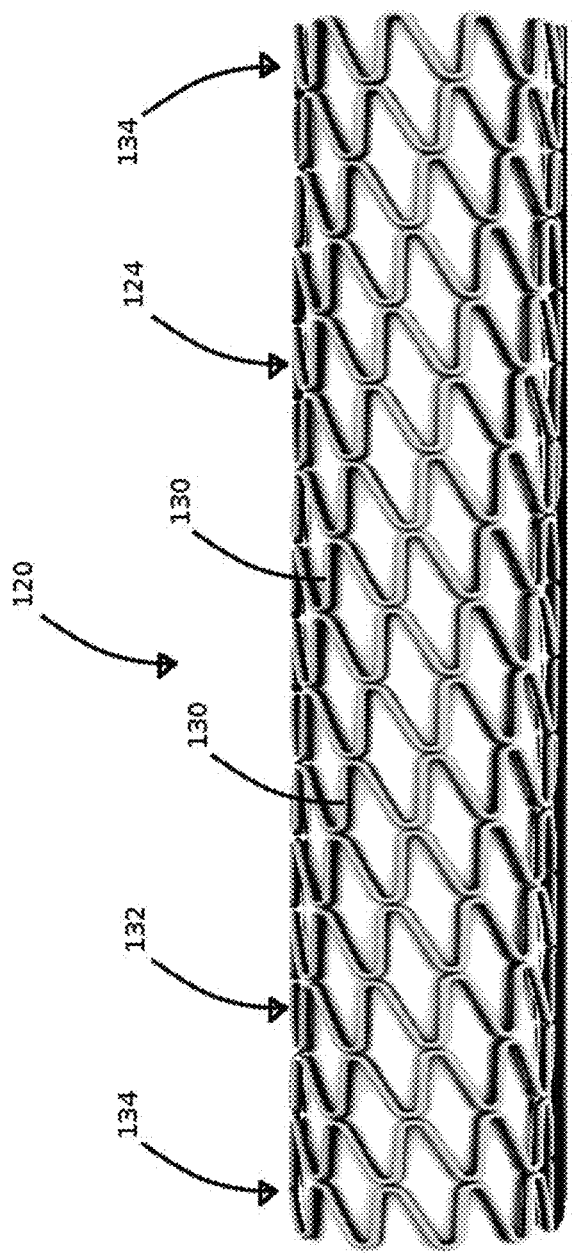
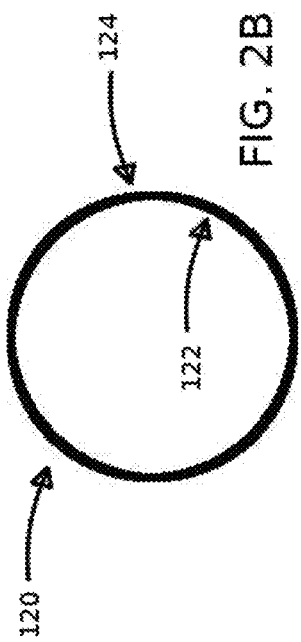

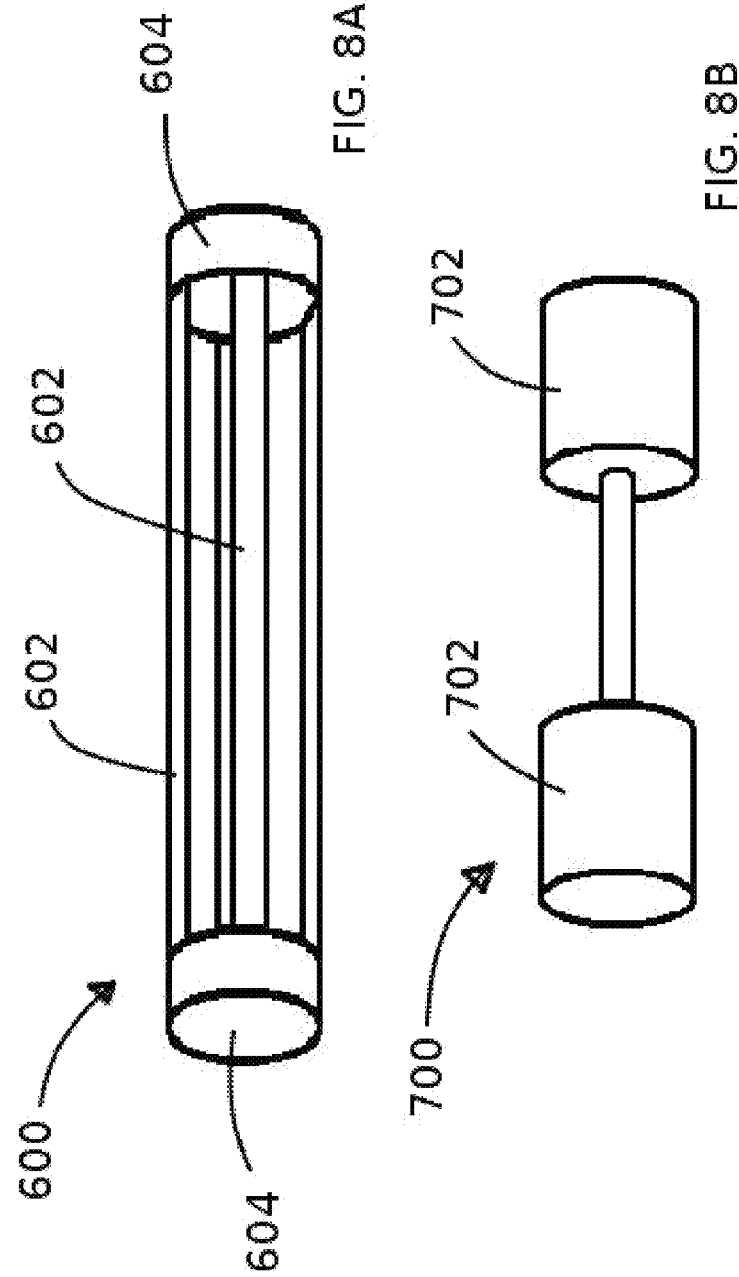

PREFERENTIALLY ELECTROPOLISHED STENT SYSTEM AND METHOD OF MANUFACTURE

TECHNICAL FIELD

The technical field of this disclosure is medical implant devices, particularly, preferentially electropolished stent systems and methods of manufacture.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz, and U.S. Pat. No. 5,421,955 to Lau. Another exemplary wire stent is the Welded Sinusoidal Wave Stent disclosed in U.S. Pat. No. 6,136,023 to Boyle. Balloon-expandable stents are mounted on a collapsed balloon at a diameter smaller than when the stents are deployed. Stents can also be self-expanding, growing to a final diameter when deployed without mechanical assistance from a balloon or like device.

Concern over the long-term effects of stents in the body has led to renewed interest in the development of bare metal stents, i.e., stents with no polymers on their exposed surfaces. During one of the final steps of fabrication, the stents are polished to provide a smooth surface that makes the stent more biocompatible and less likely to be thrombogenic. It was discovered that a polished surface also improves the trackability of the stent, i.e., the polished surface reduces the force required to deliver a stent installed on an expansion balloon through the vasculature. Unfortunately, such a polished surface also results in poor retention of the stent on the balloon: during delivery, the stent is more likely to move from its initial position on the balloon or even become dislodged from the balloon.

It would be desirable to have a preferentially electropolished stent system and method of manufacture that would overcome the above disadvantages.

SUMMARY OF THE INVENTION

One aspect of the present invention provides a stent delivery system including a catheter; a balloon operably attached to the catheter; and a stent disposed on the balloon. The stent includes an elongate body having an abluminal surface and a luminal surface; wherein the abluminal surface has an abluminal average roughness less than or equal to 0.030 microns; and the luminal surface has at least one rough portion having an luminal average roughness greater than or equal to 0.036 microns.

Another aspect of the present invention provides a stent including an elongate body having an abluminal surface and a luminal surface; wherein the abluminal surface has an abluminal average roughness less than or equal to 0.030 microns; and the luminal surface has at least one rough portion having a roughness an luminal average roughness greater than or equal to 0.036 microns.

Another aspect of the present invention provides a method of manufacturing a stent providing an electropolishing apparatus having a DC source, an electrolyte bath, and an electrode, the DC source having a positive terminal and a negative terminal, the negative terminal being operably connected to the electrode, the electrode being located in the electrolyte bath; preparing a rough stent for electropolishing; operably connecting the rough stent to the positive terminal of the DC source, the rough stent having an abluminal surface and a luminal surface; placing the rough stent in the electrolyte bath; operating the electropolishing apparatus to preferentially remove surface material from the abluminal surface without removing surface material from at least a portion of the luminal surface to electropolish the abluminal surface while maintaining surface roughness on the at least a portion of the luminal surface to produce the stent.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 2A & 2B are side and end views, respectively, of a stent with preferential electropolishing in accordance with the present invention.

FIGS. 8A & 8B are side views of mandrels for use in a method of manufacturing a stent with preferential electropolishing in accordance with the present invention.

DETAILED DESCRIPTION OF PRESENTLY PREFERRED EMBODIMENTS

Figure 1:
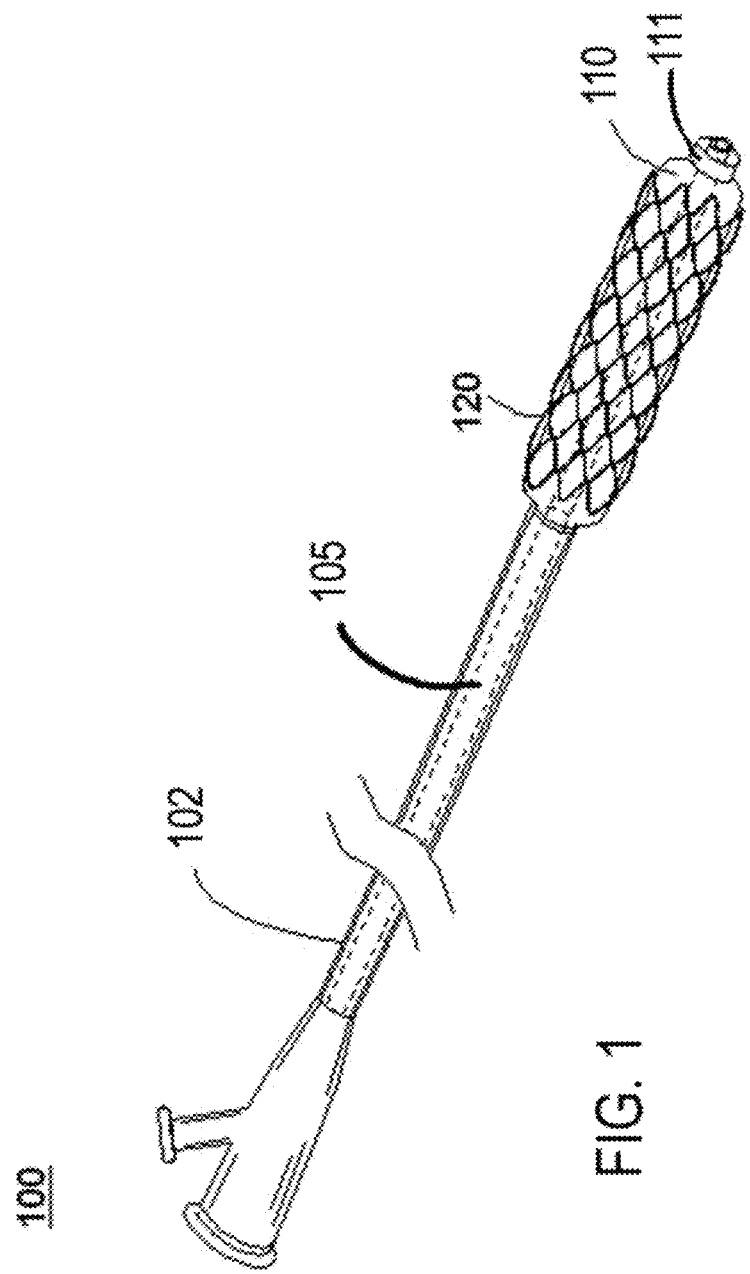
FIG. 1 is a perspective view of a stent delivery system in accordance with the present invention.

FIG. 1 is a perspective view of a stent delivery system in accordance with the present invention. The stent delivery system 100 includes a catheter 105, a balloon 110 operably attached to the catheter 105, and a stent 120 disposed on the balloon 110. The balloon 110, shown in an inflated state, can be any variety of balloons capable of expanding the stent 120. The balloon 110 can be manufactured from a material such as polyethylene, polyethylene terephthalate (PET), nylon, Pebax® polyether-block co-polyamide polymers, or the like. In one embodiment, the stent delivery system 100 can include retention means 111, such as mechanical or adhesive structures, for retaining the stent 120 on the balloon 110 until the stent 120 is deployed. The catheter 105 may be any variety of balloon catheters, such as a PTCA (percutaneous transluminal coronary angioplasty) balloon catheter, capable of supporting a balloon during angioplasty. The stent delivery system 100 can also include a sheath 102 through which the stent 120 is delivered to the deployment site.

FIGS. 2A & 2B, in which like elements share like reference numbers, are a side view and end view, respectively, of a stent with preferential electropolishing in accordance with the present invention.

In this example, the stent 120 is a continuous sinusoidal stent formed by bending a wire into a waveform having a constant frequency then wrapping the wire into a hollow cylindrical shape to form the stent 120. The stent 120 includes a number of segments 132 formed of struts 130. Longitudinally adjacent segments 132 can be fused or welded to each other to maintain the hollow cylindrical shape. The stent has ends 134.

The stent 120 is an elongate body having a luminal surface 122 facing the longitudinal axis and an abluminal surface 124 opposite the luminal surface 122. The abluminal surface 124 is electropolished to an average roughness less than or equal to 0.030 microns, and more particularly about 0.026±0.004 microns, and the luminal surface 122 has at least one rough portion with an average roughness greater than or equal to 0.036 microns, and more particularly about 0.046±0.010 microns. The luminal average roughness can exceed the abluminal average roughness by greater than or equal to 0.020 microns. The values of and the difference between the luminal average roughness and the abluminal average roughness each individually produce new and unexpected results by greatly increasing stent trackability and retention. As used herein, average roughness $R_a$ is defined as the arithmetic average of the roughness values measured with a profilometer over a standard length section of the stent. In one example, the average roughness $R_a$ can be determined in accordance with ANSI Standard B46.1. Those skilled in the art will appreciate that roughness measurements can be obtained by different methods as desired for a particular application.

The rough portion can completely cover the luminal surface 122, or rough portions can partially cover the luminal surface 122 in patterns as desired with the remainder of the luminal surface 122 which is not a rough portion being electropolished. Exemplary patterns for the rough portion include axial stripes, radial bands, or the like. In one embodiment, the pattern for the rough portion covers a longitudinal portion at the ends 134 and the middle longitudinal portion is electropolished. In one embodiment, the rough portion is selected to provide a retention force of greater than 255 grams and the abluminal average roughness is selected to provide a tracking force of less than 55.5 grams.

The stent 120 can be made from any biocompatible material which can be electropolished and used to form a stent, such as stainless steel, nickel-cobalt-chromium-molybdenum superalloy, titanium-nickel (nitinol), magnesium, steel alloys containing chromium, cobalt, tungsten, and/or iridium, titanium, cobalt-chromium-platinum, nickel-platinum, molybdenum-rhenium, tantalum, combinations of these materials, or any other biologically compatible low shape-memory material and/or can include composite layers of any of the materials listed.

Those skilled in the art will appreciate that the stent can be a continuous sinusoidal stent, a modular stent, a laser cut stent, or any other metallic stent as desired for a particular application. The continuous sinusoidal stent is formed from a single wire bent into a waveform, then wrapped into a hollow cylindrical shape and fused to form the stent. The modular stent is formed from a number of individual hoop-like stent segments fused together to form the hollow cylindrical shape. The laser cut stent is cut from a cylindrical tube to form the desired stent segments and shape.

Figure 3:
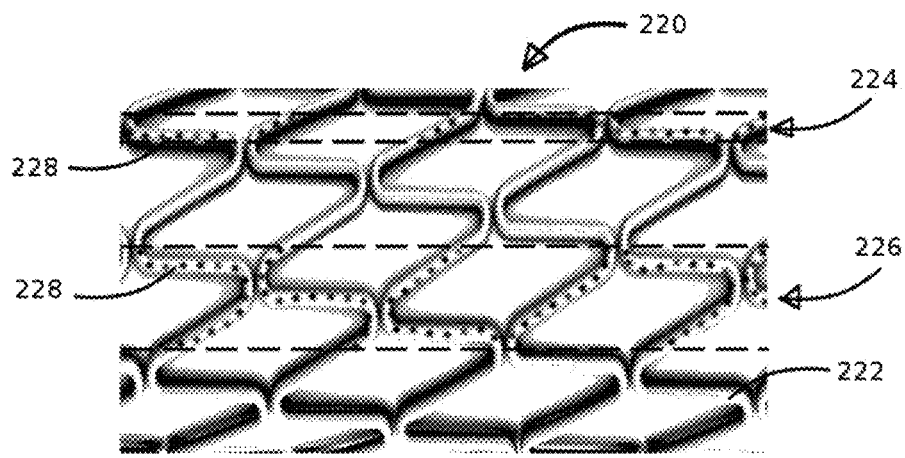
FIG. 3 is a side view of a section of a stent with axial stripes of preferential electropolishing in accordance with the present invention.

FIG. 3 is a side view of a section of a stent with axial stripes of preferential electropolishing in accordance with the present invention. In this example, the stent 220 includes rough portions 228 in axial stripes 224, 226 on the luminal surface 222. An axial stripe 224 is narrow, while axial stripe 226 is wider. Those portions of the luminal surface 222 which are not a rough portions 228 are electropolished. Those skilled in the art will appreciate that the width, number, and positioning of the axial stripes on the luminal surface 222 can be selected as desired for a particular application.

Figure 4:
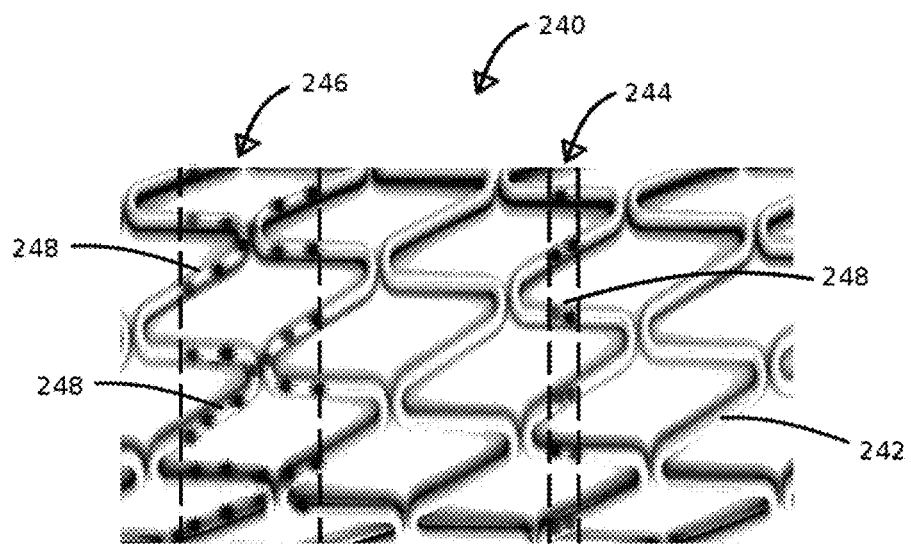
FIG. 4 is a side view of a section of a stent with radial bands of preferential electropolishing in accordance with the present invention.

FIG. 4 is a side view of a section of a stent with radial bands of preferential electropolishing in accordance with the present invention. In this example, the stent 240 includes rough portions 248 in radial bands 244, 246 on the luminal surface 242. Radial band 244 is narrow, while radial band 246 is wider. Those portions of the luminal surface 242 which are not a rough portions 248 are electropolished. Those skilled in the art will appreciate that the width, number, and positioning of the radial bands on the luminal surface 242 can be selected as desired for a particular application. In one example, radial bands are located at the ends of the stent.

Figure 5:
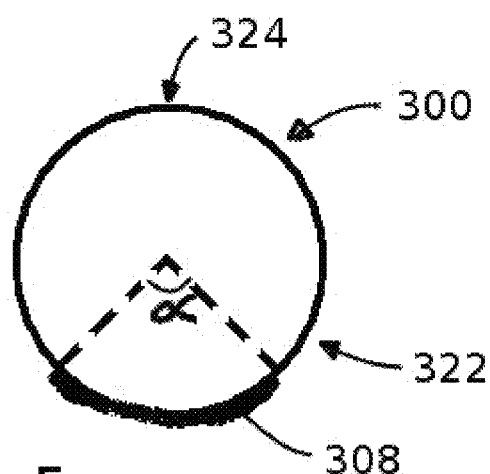
FIG. 5 is a detail cross section view of a strut of a stent with radial bands of preferential electropolishing in accordance with the present invention.

FIG. 5 is a detail cross section view of a strut of a stent with radial bands of preferential electropolishing in accordance with the present invention. In this example, the strut 300 is circular in cross-section, with a luminal surface 322 and an abluminal surface 324. A portion of the luminal surface 322 subtended by the angle $\alpha$ has a rough portion 308. The angle $\alpha$ can extend up to 180 degrees when the rough portion 308 completely covers the luminal surface 322. In one embodiment, the angle $\alpha$ is 90 degrees. Those skilled in the art will appreciate that the strut can have any cross-section profile, e.g., circular, rectangular, ellipsoidal, etc., as desired for a particular application.

Figure 6:
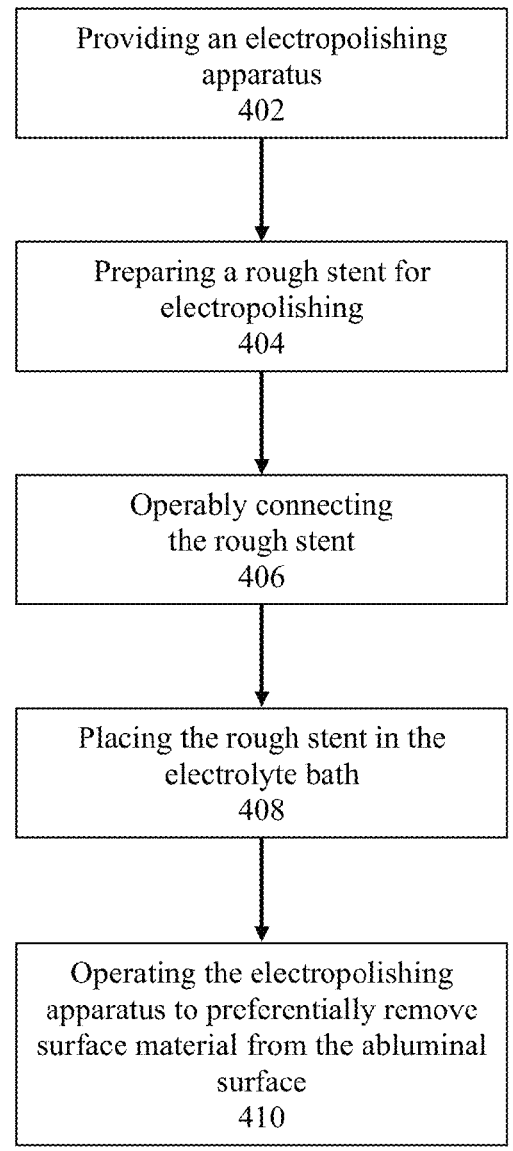
FIG. 6 is a flowchart of a method of manufacturing a stent with preferential electropolishing in accordance with the present invention.

FIG. 6 is a flowchart of a method of manufacturing a stent with preferential electropolishing in accordance with the present invention. The method 400 includes providing an electropolishing apparatus 402 having a DC source, an electrolyte bath, and an electrode, the DC source having a positive terminal and a negative terminal, the negative terminal being operably connected to the electrode, the electrode being located in the electrolyte bath; preparing a rough stent for electropolishing 404; operably connecting the rough stent 406 to the positive terminal of the DC source, the rough stent having an abluminal surface and a luminal surface; placing the rough stent in the electrolyte bath 408; operating the electropolishing apparatus to preferentially remove surface material from the abluminal surface 410 without removing surface material from at least a portion of the luminal surface to electropolish the abluminal surface while maintaining surface roughness on the at least a portion of the luminal surface to produce the stent.

The providing an electropolishing apparatus 402 can include providing an electropolishing apparatus as described in connection with FIG. 7 below. The electropolishing apparatus can be any electropolishing apparatus suitable for the stent materials.

Referring to FIG. 6, the preparing a rough stent for electropolishing 404 can include preliminary preparations of the rough stent to achieve the desired final finish. Preparations can include cleaning and degreasing, and can also include polishing and/or roughening the luminal and/or abluminal surfaces of the rough stent. The preparing 404 can also include preparing the rough stent with masks or other equipment so that the rough portions on the luminal surface of the stent occur in a desired pattern. In one embodiment, the preparing 404 can include applying a contact mask to the portion of the luminal surface, the method 400 further includes removing the contact mask after the operating 410. In another embodiment, the preparing 404 can include fixing the rough stent on a mandrel in contact with the portion of the luminal surface, and the method 400 further includes removing the mandrel from the stent after the operating. In one example, the mandrel is in contact with the portion of the luminal surface along axial stripes as illustrated in FIG. 3A. In another example, the mandrel is in contact with the portion of the luminal surface along radial bands as illustrated in FIG. 3B. Referring to FIG. 6 for another embodiment, the preparing 404 can include placing a flow reducer interior to the luminal surface, the operating 410 can include generating axial electrolyte flow past the stent, and the method 400 can further include removing the flow reducer from the stent after the operating.

After the preparing 404, the method 400 continues with the operably connecting the rough stent 406 to the positive terminal of the DC source, and the placing of the rough stent in the electrolyte bath 408.

The operating the electropolishing apparatus to preferentially remove surface material from the abluminal surface 410 can include electropolishing the abluminal surface to an average roughness less than or equal to 0.030 microns, and more particularly about 0.026±0.004 microns. The operating 410 can further include leaving at least a portion of the luminal surface with an average roughness greater than or equal to 0.036 microns, and more particularly about 0.046±0.010 microns. The operating 410 can further include electropolishing the abluminal surface so that luminal average roughness exceeds abluminal average roughness by greater than or equal to 0.020 microns. The operating 410 can remove surface material from the abluminal surface without removing surface material from at least a portion of the luminal surface, to electropolish the abluminal surface while maintaining surface roughness on the at least a portion of the luminal surface to produce the stent. The method 400 can also include post-treatment of the stent to remove chemicals and chemical byproducts from the stent.

In an alternate embodiment, the method can simultaneously electropolish both the luminal surface and the abluminal surface, then the luminal surface can be roughened to the desired roughness.

Figure 7:
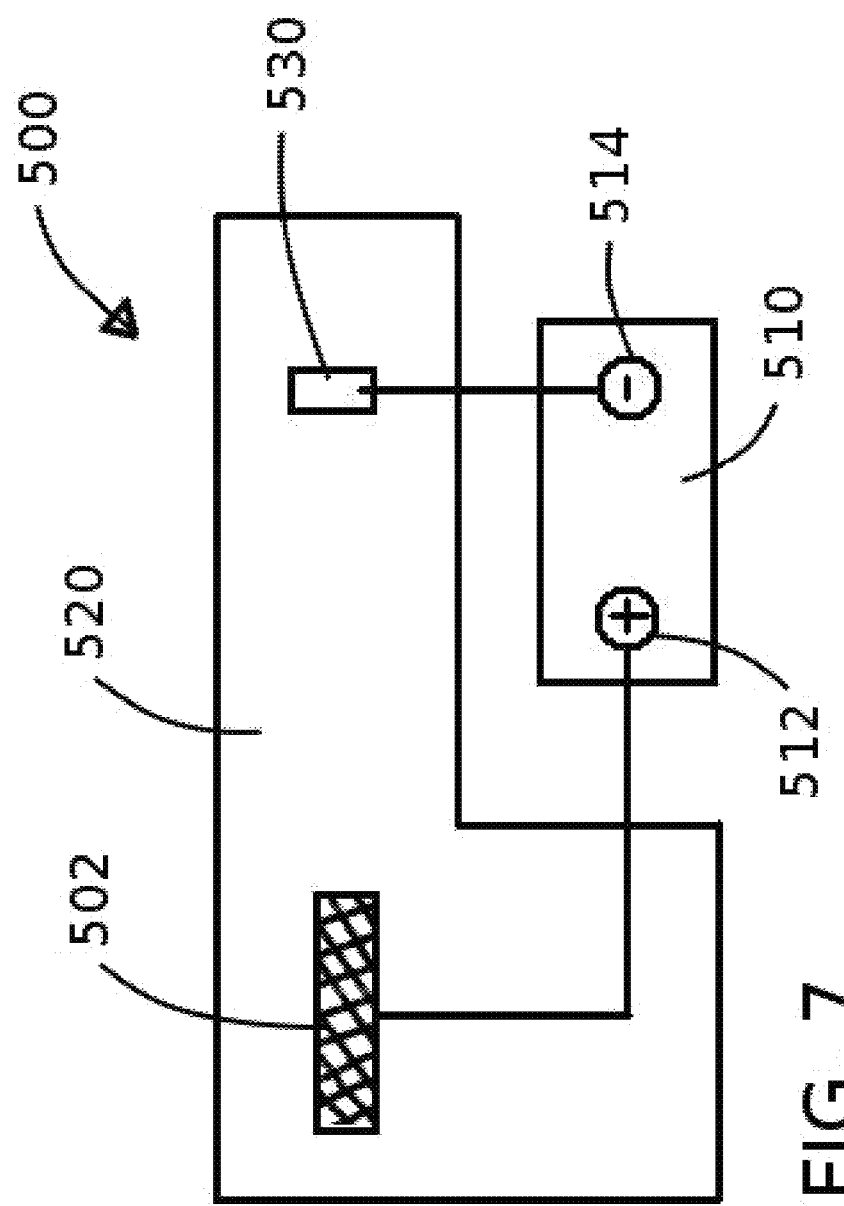
FIG. 7 is a block diagram of an apparatus for use in a method of manufacturing a stent with preferential electropolishing in accordance with the present invention.

FIG. 7 is a block diagram of an apparatus for use in a method of manufacturing a stent with preferential electropolishing in accordance with the present invention. The electropolishing apparatus 500 includes a DC source 510, an electrolyte bath 520, and an electrode 530. The DC source 510 has a positive terminal 512 operably connected to the stent 502 and a negative terminal 514 operably connected to the electrode 530, which is located in the electrolyte bath 520. The stent 502 acts as the anode and the electrode 530 acts as the cathode with current passing from the stent 502 to the electrode 530

In one exemplary apparatus and process for cobalt alloys, such as a cobalt alloy including approximately 20% chromium, 35% nickel, 10% molybdenum, and the balance cobalt, the electrolyte bath 520 is 75% commercial phosphoric acid and 25% concentrated sulfuric acid at 100° F. The metal in the electrolyte bath 520 is maintained below 3 weight percent and the specific gravity of the electrolyte bath 520 held above 1.7. Copper contacts are used for the electrode 530 and to hold the stent 502. The current density is maintained between 50 and 100 asf (amps per square foot). Those skilled in the art will appreciate that the apparatus and process can be selected as desired for a particular metal or alloy.

FIGS. 8A & 8B are side views of mandrels for use in a method of manufacturing a stent with preferential electropolishing in accordance with the present invention. A mandrel can be placed in contact with the luminal surface of the rough stent to reduce or prevent electropolishing at the points of contact. The fraction of the rough portion remaining on the stent can be selected to tune the retention of the stent on the balloon as desired.

Referring to FIG. 8A, the mandrel body 600 includes mandrel axial stripes 602 positioned between ends 604. During electropolishing, the rough stent is fixed on the mandrel body 600 so that the mandrel axial stripes 602 are in contact with the luminal surface of the rough stent. The contact prevents the electropolishing of those portions of the luminal surface, resulting in rough portions on the luminal surface. The mandrel body 600 can be hard or resilient as desired for a particular application. The more resilient the mandrel body 600, the larger the angle of the rough portion on each strut of the stent. Those skilled in the art will appreciate that the width, number, and positioning of the mandrel axial stripes 602 can be selected as desired to produce the desired width, number, and positioning of axial stripes on the luminal surface of the stent.

Referring to FIG. 8B, the mandrel body 700 includes mandrel radial bands 702. During electropolishing, the rough stent is fixed on the mandrel body 700 so that the mandrel radial bands 702 are in contact with the luminal surface of the rough stent. The contact prevents the electropolishing of those portions of the luminal surface, resulting in rough portions on the luminal surface. The mandrel body 700 can be hard or resilient as desired for a particular application. The more resilient the mandrel body 700, the larger the angle of the rough portion on each strut of the stent. Those skilled in the art will appreciate that the width, number, and positioning of the mandrel radial bands 702 can be selected as desired to produce the desired width, number, and positioning of radial bands on the luminal surface of the stent.

Figure 9A:
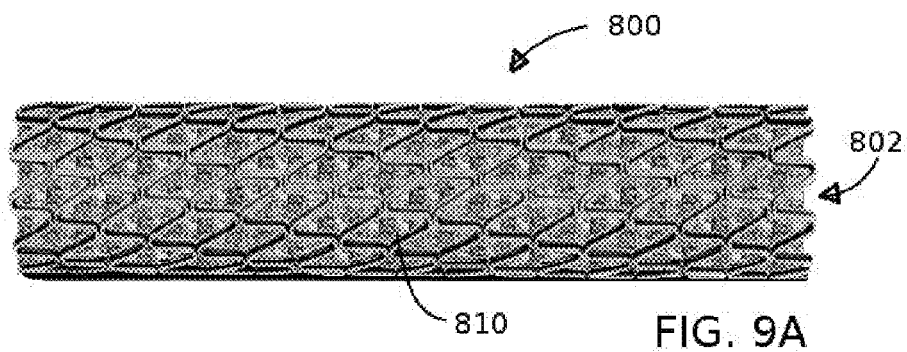
FIGS. 9A & 9B are side views of stents with flow restrictors for use in a method of manufacturing a stent with preferential electropolishing in accordance with the present invention.
Figure 9B:
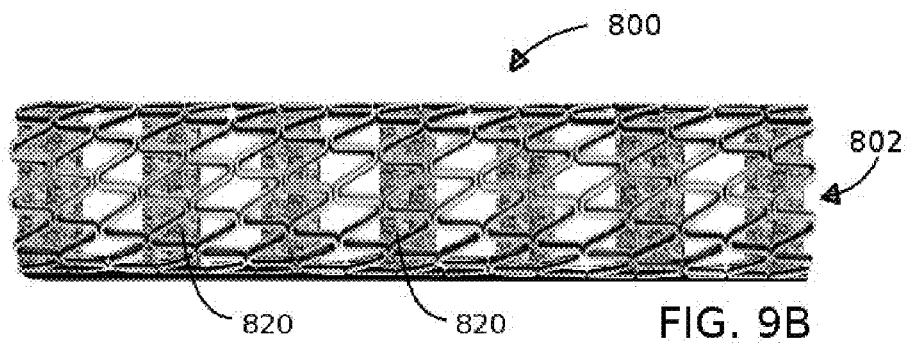

FIGS. 9A & 9B are side views of stents with flow restrictors for use in a method of manufacturing a stent with preferential electropolishing in accordance with the present invention. Flow reducers can be placed within the lumen of the rough stent to reduce flow of the electrolyte through the lumen, thus reducing electropolishing on the luminal surface of the rough stent compared to the abluminal surface. The amount of electropolishing allowed on the luminal surface can be selected to tune the retention of the stent on the balloon as desired.

Referring to FIG. 9A, the stent 800 includes a flow reducer 810 within the lumen 802 of the rough stent 800. The flow reducer 810 can be a fibrous or sponge material that is compatible with the materials of the stent 800 and the electropolishing process. During electropolishing, flow is induced around the rough stent 800, such as flow parallel or perpendicular to the axis of the rough stent 800. In one example, the flow is induced by pumping the electrolyte past the rough stent 800. In another example, the flow is induced by repeatedly dipping the rough stent 800 in and out of the electrolyte. The flow reducer 810 reduces the flow of the electrolyte in the lumen 802 of the rough stent 800, preventing or reducing electropolishing of the luminal surface.

Referring to FIG. 9B, the stent 800 includes a number of flow reducers 820 within the lumen 802 of the rough stent 800 along the longitudinal central axis of the rough stent 800. The flow reducers 820 can be a fibrous or sponge material that is compatible with the materials of the stent 800 and the electropolishing process. During electropolishing, flow is induced around the rough stent 800, such as flow parallel or perpendicular to the axis of the rough stent 800. In one example, the flow is induced by pumping the electrolyte past the rough stent 800. In another example, the flow is induced by repeatedly dipping the rough stent 800 in and out of the electrolyte. The flow reducers 820 reduce the flow of the electrolyte bath in the lumen 802 of the rough stent 800, preventing or reducing electropolishing of the luminal surface where the flow reducers 820 are present. In this example, the flow reducers 820 produce rough portions in radial bands. Those skilled in the art will appreciate that the width, number, and positioning of the flow reducers 820 can be selected as desired to produce the desired width, number, and positioning of radial bands on the luminal surface of the stent.

In another embodiment, rough portions on the luminal surface of the stent can be retained by applying a contact mask to the luminal surface. The mask can be any device which prevents or reduces the electrolyte contact with the luminal surface. In one example, the mask is a tape applied to the luminal surface. In another example, the mask is a temporary coating sprayed, rolled, or painted onto the luminal surface. After electropolishing, the mask can be removed by physically stripping the mask from the luminal surface or chemically dissolving the mask.

EXPERIMENTS

Figure 10A:
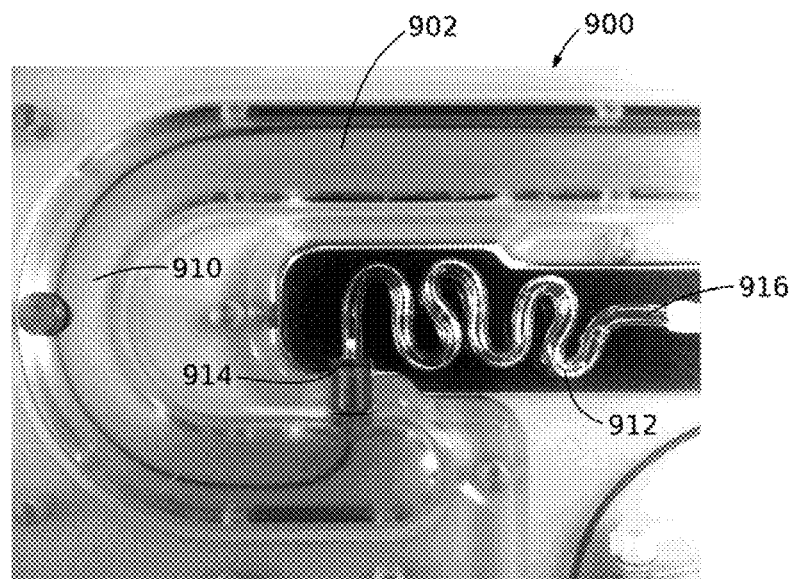
FIGS. 10A & 10B are a side view of a test fixture and schematic drawing of a tracking path section, respectively, for measuring trackability of a stent with preferential electropolishing in accordance with the present invention.
Figure 10B:
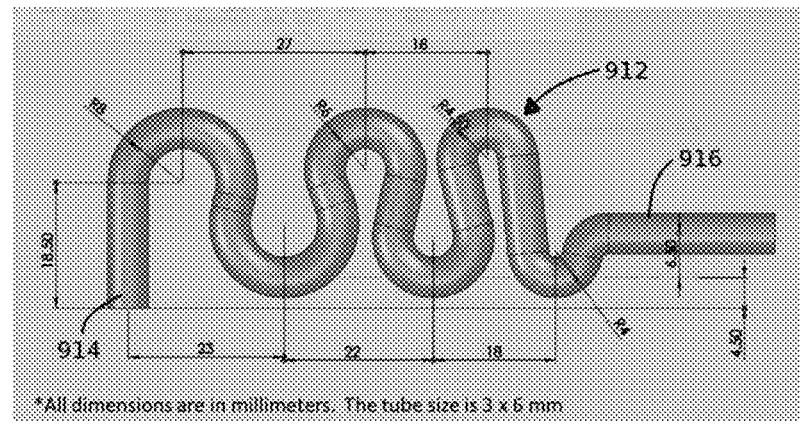

FIGS. 10A & 10B are a side view of a test fixture and schematic drawing of a tracking path section, respectively, for measuring trackability of a stent with preferential electropolishing in accordance with the present invention. The trackability test fixture 900 determines trackability by measuring the force required to push the stent installed on a balloon through a two-dimensional track having a number of bands and a tortuous section.

The trackability test fixture 900 includes the track 902 having an aortic arch section 912 and a tracking path section 914. The track 902 is formed from glass and lies in a single plane. The track 902 has inner diameters approximating the diameters of the vasculature in which the stent delivery system will be used. The aortic arch section 912 models the aortic arch and the tracking path section 914 models the tortuous vasculature of smaller vessels. In one example, the tracking path section 914 has an inner diameter of 3 millimeters and an outer diameter of 6 millimeters. The tracking path section 914 includes a number of alternating curves of various radii. In one example as shown in FIG. 10B, the tracking path section 914 has six curves with radii of curvature between four and eight times the radius of the tubing. Those skilled in the art will appreciate that the dimensions provided in FIG. 10B are exemplary and that a trackability test fixture having other dimensions can be used to determine stent trackability.

During testing as illustrated in FIG. 10A, a guide catheter is advanced through the aortic arch section 910 of the track 902 until the distal end of the guide catheter is at the proximal end 914 of the tracking path section 912. A guide wire is advanced through the guide catheter and through the tracking path section 912 of the track 902 until the distal end of the guide wire is past the distal end 916 of the tracking path section 912. A stent on a balloon catheter is advanced over the guide wire and through the tracking path section 912 until the distal end of the stent is at the proximal end 914 of the tracking path section 912. To measure trackability, the stent is advanced through the tracking path section 912 while measuring the force required to advance the stent delivery system. The testing is terminated when the distal end of the stent reaches the distal end 916 of the tracking path section 912. The experimental trackability results below were measured using a trackability test fixture as described in conjunction with FIGS. 10A & 10B.

The experimental retention results below were measured using a test fixture that determines the force required to dislodge a stent from a balloon. To test stent retention, the stent under test was crimped on the balloon of a balloon catheter in the normal manner. The proximal end of the stent was butted against a V-block and the balloon catheter pulled until the force was sufficient to either dislodge the stent from the balloon or to deform the stent itself. The force applied to the balloon catheter was measured by a load cell and the failure force gF (grams force) required to dislodge or deform the stent recorded.

Experimental Results

Outer Surface Roughness

Figure 11A:
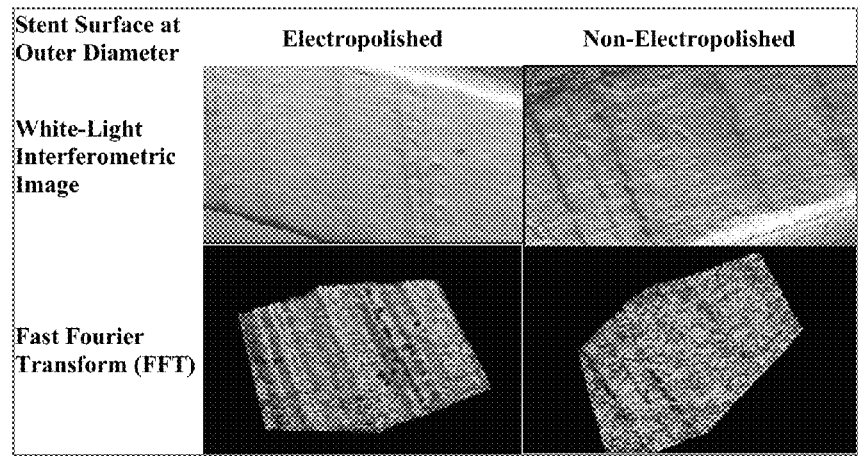
FIGS. 11A & 11B are surface images and graphs of experimental results, respectively, for stent outer diameters with and without electropolishing.
Figure 11B:
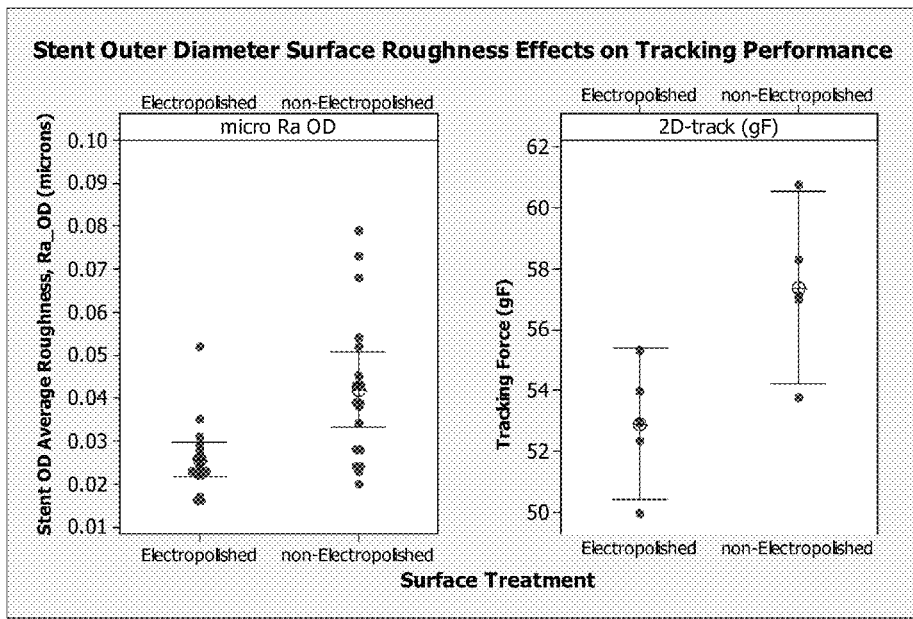

FIGS. 11A & 11B are surface images and graphs of experimental results, respectively, for stent outer diameters with and without electropolishing. The experiment provided the new and unexpected result of a 7 percent reduction in tracking force for stents with electropolished outer diameters. The roughness measurements in this experiment were obtained by white-light interferometry with a 7 micron high-pass Fast Fourier Transform (FFT) filter applied to isolate nano-roughness. Those skilled in the art will appreciate that roughness measurements can be obtained by different methods as desired for a particular application.

Referring to FIG. 11A, white-light interferometric images in the electropolished state and the non-electropolished state are provided for the stent surfaces at an outer diameter. Corresponding Fast Fourier Transform (FFT) images in the electropolished state and the non-electropolished state are provided for the stent surfaces at an outer diameter. The values of Stent OD Average Surface Roughness, Ra_OD, presented in the graph of FIG. 11B is calculated from the FFT data represented by the FFT images.

In this experiment, the stents are continuous sinusoidal stents made of core wire material with cobalt alloy as the shell material on the outer diameter and having a strut width of 0.0040 inches and a strut thickness of 0.0033 inches. Both the electropolished group and the non-electropolished group were started from the same stent lot. Prior to the electropolishing process, the stent lot was split into two groups: one group of fifteen stents was electropolished and the other group of fifteen stents was not. For the electropolished group, the stents were electropolished by multiple short submersions in a temperature-controlled acid solution bath at 95 degrees Fahrenheit, with a voltage of 6.5 Volt passing through the electropolishing system. The stents were subsequently rinsed and passivated. For both groups, five samples were evaluated for deliverability and stent retention testing, and three samples were evaluated for surface roughness. Surface roughness was evaluated at both inner diameter and outer diameter at multiple locations along the stent, i.e., the crown and strut area at the middle and end region of the stent. All stents were crimped on catheters from the same catheter lot with the same crimper setting. All experiments were performed with the same test setup to minimize any test method setup variations. Referring to the graph of Stent OD Average Surface Roughness, Ra_OD, presented in FIG. 11B, the OD Average Roughness for the electropolished stents is 0.026 microns with a 95 percent confidence interval (about two sigma) between 0.022 microns and 0.030 microns. The OD Average Roughness for the non-electropolished stents is 0.042 microns with a 95 percent confidence interval between 0.033 microns and 0.051 microns.

The experimental results show that a stent with an electropolished abluminal surface has better tracking than a stent in which the abluminal surface is rough. For electropolished stents in this experiment, the whole stent including both the luminal surface and the abluminal surface was electropolished. The experimental results are valid for a stent which is preferentially electropolished on the abluminal surface versus the luminal surface because only the abluminal surface is in contact with the vasculature.

The stent trackability was tested as described in conjunction with FIG. 10 above. Referring to FIG. 11B, the Tracking Force for the electropolished stents is about 53 grams Force (gF) on average with a 95 percent confidence interval of about 50 gF and about 55 gF. The Tracking Force for the non-electropolished stents is about 57 grams Force (gF) on average with a 95 percent confidence interval of about 54 gF and about 60 gF. Electropolishing the abluminal surface reduces the Tracking Force by about 7 percent.

Thus, the stents with electropolishing had better trackability results as demonstrated by a lower force being required to advance the electropolished stent through the track. The stents with electropolishing have an abluminal surface roughness less than or equal to 0.030 microns, and more particularly about 0.026±0.004 microns.

Experimental Results

Inner Surface Roughness

Figure 12A:
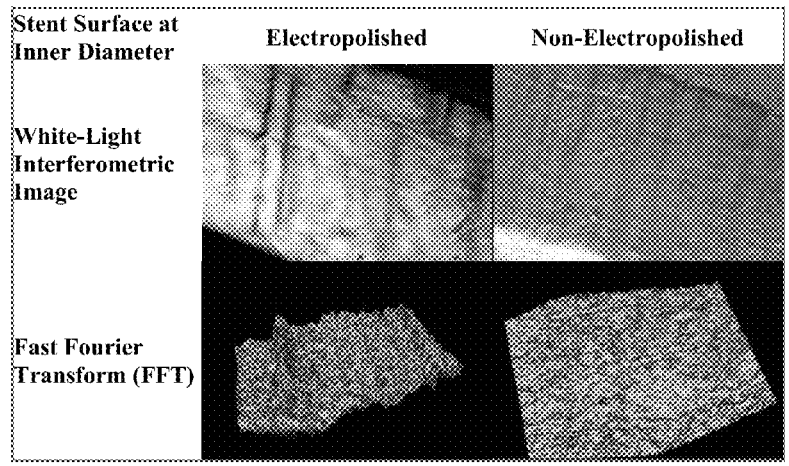
FIGS. 12A & 12B are surface images and graphs of experimental results, respectively, for stent inner diameters with and without electropolishing.
Figure 12B:
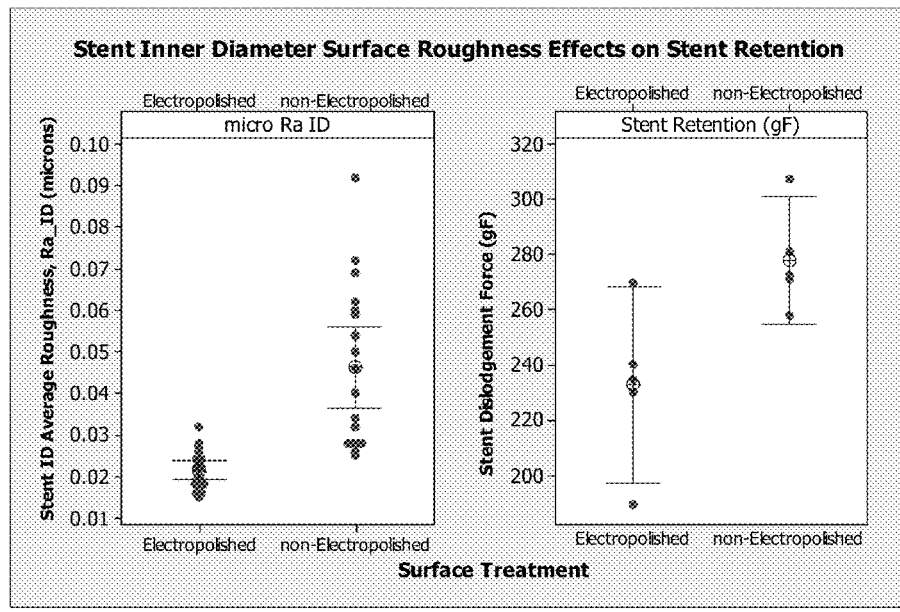

FIGS. 12A & 12B are surface images and graphs of experimental results, respectively, for stent inner diameters with and without electropolishing. The experiment provided the new and unexpected result of a 19 percent increase in retention force for stents with unpolished inner diameters. The roughness measurements in this experiment were obtained by white-light interferometry with a 7 micron high-pass Fast Fourier Transform (FFT) filter applied to isolate nano-roughness. Those skilled in the art will appreciate that roughness measurements can be obtained by different methods as desired for a particular application.

Referring to FIG. 12A, white-light interferometric images in the electropolished state and the non-electropolished state are provided for the stent surfaces at an inner diameter. Corresponding Fast Fourier Transform (FFT) images in the electropolished state and the non-electropolished state are provided for the stent surfaces at an inner diameter. The values of Stent ID Average Surface Roughness, Ra_ID, presented in the graph of FIG. 12B is calculated from the FFT data represented by the FFT images.

In this experiment, the stents are continuous sinusoidal stents made of core wire material with cobalt alloy as the shell material on the outer diameter and having a strut width of 0.0040 inches and a strut thickness of 0.0033 inches. Both the electropolished group and the non-electropolished group were started from the same stent lot. Prior to the electropolishing process, the stent lot was split into two groups: one group of fifteen stents was electropolished and the other group of fifteen stents was not. For the electropolished group, the stents were electropolished by multiple short submersions in a temperature-controlled acid solution bath at 95 degrees Fahrenheit, with a voltage of 6.5 Volt passing through the electropolishing system. The stents were subsequently rinsed and passivated. For both groups, five samples were evaluated for deliverability and stent retention testing, and three samples were evaluated for surface roughness. Surface roughness was evaluated at both inner diameter and outer diameter at multiple locations along the stent, i.e., the crown and strut area at the middle and end region of the stent. All stents were crimped on catheters from the same catheter lot with the same crimper setting. All experiments were performed with the same test setup to minimize any test method setup variations. Referring to the graph of Stent ID Average Surface Roughness, Ra_ID, presented in FIG. 12B, the ID Average Roughness for the electropolished stents is 0.022 microns with a 95 percent confidence interval (about two sigma) between 0.019 microns and 0.024 microns. The ID Average Roughness for the non-electropolished stents is 0.046 microns with a 95 percent confidence interval between 0.037 microns and 0.056 microns.

The experimental results show that a stent with an unpolished luminal surface will have better retention on a balloon than a stent in which the luminal surface is electropolished. For electropolished stents in this experiment, the whole stent including both the luminal surface and the abluminal surface was electropolished. The experimental results are valid for a stent which is preferentially electropolished on the abluminal surface versus the luminal surface because only the luminal surface is in contact with the balloon.

Referring to FIG. 12B, the Stent Dislodgement Force for the electropolished stents is about 230 grams Force (gF) on average with a 95 percent confidence interval of about 200 gF and about 270 gF. The Stent Dislodgement Force for the non-electropolished stents is about 280 grams Force (gF) on average with a 95 percent confidence interval of about 255 gF and about 300 gF. Leaving the luminal surface of the stent unpolished increases the Stent Dislodgement Force to provide better retention by about 19 percent.

Thus, the stents without electropolishing had consistently better stent retention results as demonstrated by a higher force being required to dislodge or deform the stent from the balloon. The stents without electropolishing have a luminal surface roughness greater than or equal to 0.036 microns, and more particularly about 0.046±0.010 microns.

In one embodiment, the experimental results for outer surface roughness described in conjunction with FIGS. 11A & 11B and the experimental results for inner surface roughness described in conjunction with FIGS. 12A & 12B can be combined. The difference between the luminal average roughness and the abluminal average roughness produces new and unexpected results by greatly increasing stent trackability and retention. In one embodiment, the luminal average roughness can exceed the abluminal average roughness by greater than or equal to 0.020 microns, regardless of the particular values of the luminal average roughness and the abluminal average roughness.

It is important to note that FIGS. 1-12 illustrate specific applications and embodiments of the present invention, and are not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A stent delivery system comprising:
a catheter;
a balloon operably attached to the catheter; and
a stent disposed on the balloon;
wherein the stent comprises:
an elongate body having an abluminal surface and a luminal surface;
wherein the abluminal surface has an abluminal average roughness less than or equal to 0.030 microns; and
the luminal surface has at least one rough portion having a luminal average roughness greater than or equal to 0.036 microns.

2. The stent delivery system of claim 1 wherein the rough portion completely covers the luminal surface.

3. The stent delivery system of claim 1 wherein the elongate body comprises a single wire having a circumference and being formed into the stent, the rough portion covering 90 degrees of the circumference on the luminal surface.

4. The stent delivery system of claim 1 wherein the rough portion comprises axial stripes on the luminal surface.

5. The stent delivery system of claim 1 wherein the rough portion comprises radial bands on the luminal surface.

6. The stent delivery system of claim 1 wherein the luminal average roughness is selected to provide a retention force of greater than 255 grams and the abluminal average roughness is selected to provide a tracking force of less than 55.5 grams.

7. The stent delivery system of claim 1 wherein the abluminal average roughness is 0.026±0.004 microns and the luminal average roughness is 0.046±0.010 microns.

8. The stent delivery system of claim 1 wherein the luminal average roughness exceeds the abluminal average roughness by greater than or equal to 0.020 microns.

9. The stent delivery system of claim 1 wherein the stent is selected from the group consisting of a continuous sinusoidal stent, a modular stent, and a laser cut stent.

10. A stent comprising:
an elongate body having an abluminal surface and a luminal surface;
wherein the abluminal surface has an abluminal average roughness less than or equal to 0.030 microns; and
the luminal surface has at least one rough portion having a roughness a luminal average roughness greater than or equal to 0.036 microns.

11. The stent of claim 10 wherein the rough portion completely covers the luminal surface.

12. The stent of claim 10 wherein the elongate body comprises a single wire having a circumference and being formed into the stent, the rough portion covering 90 degrees of the circumference on the luminal surface.

13. The stent of claim 10 wherein the rough portion comprises axial stripes on the luminal surface.

14. The stent of claim 10 wherein the rough portion comprises radial bands on the luminal surface.

15. The stent of claim 10 wherein the luminal average roughness is selected to provide a retention force of greater than 255 grams and the abluminal average roughness is selected to provide a tracking force of less than 55.5 grams.

16. The stent of claim 10 wherein the abluminal average roughness is 0.026±0.004 microns and the luminal average roughness is 0.046±0.010 microns.

17. The stent of claim 10 wherein the luminal average roughness exceeds the abluminal average roughness by greater than or equal to 0.020 microns.

18. The stent of claim 10 wherein the stent is selected from the group consisting of a continuous sinusoidal stent, a modular stent, and a laser cut stent.

* * * * *